(12) United States Patent
Shortt et al.

(10) Patent No.: US 10,082,470 B2
(45) Date of Patent: Sep. 25, 2018

(54) DEFECT MARKING FOR SEMICONDUCTOR WAFER INSPECTION

(71) Applicant: KLA-Tencor Corporation, Milpitas, CA (US)

(72) Inventors: David Shortt, Los Gatos, CA (US); Steven Lange, Alamo, CA (US); Junwei Wei, Milpitas, CA (US); Daniel Kapp, Pleasanton, CA (US); Charles Amsden, Mountain View, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/430,817

(22) Filed: Feb. 13, 2017

(65) Prior Publication Data

US 2018/0088056 A1 Mar. 29, 2018

Related U.S. Application Data

(60) Provisional application No. 62/400,182, filed on Sep. 27, 2016.

(51) Int. Cl.
*G01N 1/44* (2006.01)
*G01N 21/95* (2006.01)
(Continued)

(52) U.S. Cl.
CPC ......... *G01N 21/8851* (2013.01); *G01N 1/286* (2013.01); *G01N 1/44* (2013.01); *G01N 21/8806* (2013.01); *G01N 21/9501* (2013.01)

(58) Field of Classification Search
CPC ........... G01N 21/9501; G01N 21/8806; G01N 21/4788; G01N 21/95607; G01N 21/84;
(Continued)

(56) References Cited

U.S. PATENT DOCUMENTS

| 5,608,526 A | 3/1997 | Piwonka-Corle et al. |
| 5,859,424 A | 1/1999 | Norton et al. |

(Continued)

FOREIGN PATENT DOCUMENTS

| JP | 5425593 B2 | 2/2014 |
| JP | 5882381 B2 | 3/2016 |

OTHER PUBLICATIONS

International Search Report dated Jan. 8, 2018, for PCT Application No. PCT/US2017/053540 filed on Sep. 26, 2017 by KLA-Tencor Corporation, 3 pages.

*Primary Examiner* — Sang Nguyen
(74) *Attorney, Agent, or Firm* — Spano Law Group; Joseph S. Spano

(57) ABSTRACT

Methods and systems for accurately locating buried defects previously detected by an inspection system are described herein. A physical mark is made on the surface of a wafer near a buried defect detected by an inspection system. In addition, the inspection system accurately measures the distance between the detected defect and the physical mark in at least two dimensions. The wafer, an indication of the nominal location of the mark, and an indication of the distance between the detected defect and the mark are transferred to a material removal tool. The material removal tool (e.g., a focused ion beam (FIB) machining tool) removes material from the surface of the wafer above the buried defect until the buried defect is made visible to an electron-beam based measurement system. The electron-beam based measurement system is subsequently employed to further analyze the defect.

21 Claims, 7 Drawing Sheets

(51) Int. Cl.
*G01N 21/88* (2006.01)
*G01N 1/28* (2006.01)

(58) Field of Classification Search
CPC ..... G01N 2021/95615; G01N 21/8851; G01B 21/30; G03F 7/70625; G06F 19/00; G06F 17/40
See application file for complete search history.

(56) References Cited

U.S. PATENT DOCUMENTS

| | | | |
|---|---|---|---|
| 6,201,601 B1 | 3/2001 | Vaez-Iravani et al. | |
| 6,208,411 B1 | 3/2001 | Vaez-Iravani | |
| 6,271,916 B1 | 8/2001 | Marxer et al. | |
| 6,429,943 B1 | 8/2002 | Opsal et al. | |
| 7,027,142 B2 | 4/2006 | Some | |
| 7,130,039 B2 | 10/2006 | Vaez-Iravani et al. | |
| 7,295,303 B1 | 11/2007 | Vaez-Iravani et al. | |
| 7,478,019 B2 | 1/2009 | Langooie et al. | |
| 7,777,876 B2 | 8/2010 | Horai et al. | |
| 7,933,026 B2 | 4/2011 | Opsal et al. | |
| 8,912,495 B2 | 12/2014 | Lange | |
| 9,007,581 B2 | 4/2015 | Horai et al. | |
| 9,075,027 B2 | 7/2015 | Lange | |
| 9,164,371 B2 * | 10/2015 | Kamo | G03F 1/24 |
| 9,696,264 B2 * | 7/2017 | Lange | G01N 21/9501 |
| 2008/0015802 A1 * | 1/2008 | Urano | G01N 21/4738 702/81 |
| 2014/0111791 A1 | 4/2014 | Manassen et al. | |
| 2014/0139830 A1 * | 5/2014 | Lange | G01N 21/9501 356/237.5 |
| 2014/0165236 A1 | 6/2014 | Budach et al. | |
| 2014/0172394 A1 | 6/2014 | Kuznetsov et al. | |
| 2014/0222380 A1 | 8/2014 | Kuznetsov et al. | |
| 2014/0233024 A1 * | 8/2014 | Taniguchi | G01N 21/9501 356/237.5 |
| 2014/0268117 A1 | 9/2014 | Kolchin et al. | |
| 2014/0300890 A1 * | 10/2014 | Lange | G01N 21/9501 356/51 |
| 2015/0069241 A1 | 3/2015 | Lange | |
| 2016/0153914 A1 * | 6/2016 | Lange | G01N 21/8806 356/237.5 |

* cited by examiner

DEFECT MARKING FOR SEMICONDUCTOR WAFER INSPECTION

CROSS REFERENCE TO RELATED APPLICATION

The present application for patent claims priority under 35 U.S.C. § 119 from U.S. provisional patent application Ser. No. 62/400,182, filed Sep. 27, 2016, entitled "Defect Marking for Semiconductor Wafer Inspection," the subject matter of which is incorporated herein by reference in its entirety.

TECHNICAL FIELD

The described embodiments relate to systems for surface inspection, and more particularly to semiconductor wafer inspection modalities.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects while maintaining high throughput. In addition, memory and logic architectures are transitioning from two dimensional floating-gate architectures to fully three dimensional geometries. In some examples, film stacks and etched structures are very deep (e.g., three micrometers in depth, and more). Measurement of defects buried within these structures is critical to achieve desired performance levels and device yield, yet these measurement have proven challenging for traditional measurement systems and techniques.

In some examples, electronic tests are employed to detect buried defects. However, multiple device layers must be fabricated before electronic tests are performed. Thus, defects cannot be detected early in the production cycle. As a result, electronic tests are prohibitively expensive to perform, particularly during research and development and ramp phases of the production process, where rapid assessment of defects is critical.

In some other examples, wafers are de-processed to uncover buried defects. Wafer de-processing destroys the wafer by removing layers to reveal defects-of-interest (DOI) detected using traditional optical or electron beam inspection. This approach is very slow, requires alternate process flows at each layer, and the alternate processes may produce defects that interfere with DOI detection. In addition, some DOI on some layers are not easily revealed by wafer de-processing.

In some other examples, buried defects can be detected based on x-ray based measurement techniques. For example, an x-ray diffractive measurement system or a coherent x-ray imaging system may be employed to detect buried defects. X-ray based measurement techniques have the advantage of being non-destructive, but throughput remains quite low.

In some other examples, electron beam inspection (EBI) is employed directly to detect buried defects. However, EBI is extremely limited in its ability to detect defects beyond a depth of approximately one micrometer. In many examples, EBI is limited to depths that are far less than one micrometer (e.g., less than fifty nanometers). This limitation is due to practical limits on electron dosage before sample distortion or destruction occurs. Thus, EBI is limited in its effectiveness as a defect detection tool for thick, three dimensional structures.

Some traditional optical inspection techniques have proven effective for the detection of defects buried in relatively thick layers. In one example, confocal optical inspection is employed at different depths of focus. Confocal imaging eliminates spurious or nuisance optical signals from structures above and below the focal plane. The confocal optical inspection technique is described in further detail in U.S. Patent Publication No. 2014/0300890, which is incorporated herein by reference in its entirety. In another example, a rotating illumination beam is employed to detect buried defects in relatively thick layers. Optical inspection utilizing a rotating illumination beam is described in further detail in U.S. Patent Publication No. 2014/0268117, which is incorporated herein by reference in its entirety. In another example, different illumination wavelength ranges are employed to detect buried defects as described in further detail in U.S. Pat. No. 9,075,027, which is incorporated herein by reference it its entirety. In yet another example, multiple discrete spectral bands are employed to detect buried defects as described in further detail in U.S. Pat. No. 8,912,495, which is incorporated herein by reference it its entirety.

Although traditional optical inspection techniques have proven useful for detecting possible defects in thick layers, the measurement results are typically insufficient to identify the defect as a defect of interest and classify the defect with a high degree of confidence.

In some examples, the optical measurement results are accepted without verification. However, making process decisions based on unverified optical measurement results runs the risk of introducing process errors that lead to lost time and resources.

In some examples, an optical inspection tool records the location of defects detected on a wafer. The wafer is subsequently transferred to a focused ion beam (FIB) machining tool, along with the recorded locations. The FIB tool machines away layers of wafer material to reveal the potential defects-of-interest (DOI). The potential DOIs are subsequently inspected by traditional optical or electron beam inspection techniques (e.g., scanning electron microscopy).

Unfortunately, the rate of material removal of a FIB tool is very low. In addition, the FIB tool is limited in its ability to locate the optically detected defects with an accuracy of approximately one micrometer. Due to this uncertainty, a significant amount of time is required to machine away material before the actual defect location is identified. Typically, FIB processing of one defect requires approximately one hour, if the defect can be found at all.

Improvements in the detection of defects of interest buried in vertical semiconductor devices, such as 3D memory, VNAND memory, or other vertical structures, are desired.

SUMMARY

Methods and systems for accurately locating buried defects previously detected by an optical or x-ray inspection system are described herein. In one aspect, a physical mark is made on the surface of a wafer near a buried defect detected by an inspection system. The inspection system is also employed to accurately measure the distance between the detected defect and the physical mark in at least two dimensions.

The wafer, an indication of the nominal location of the mark, and an indication of the distance between the detected defect and the mark are transferred to another wafer processing system that includes a material removal tool and an electron-beam based measurement system. The electron-beam based measurement system cannot directly detect or verify defects buried in relatively thick semiconductor structures. But, the system is able to accurately locate the physical mark on the surface of the wafer. After accurately locating the physical mark, the electron-beam based system is able to accurately locate the buried defect based on the distance between the detected defect and the physical mark received from the inspection system. The material removal tool (e.g., a focused ion beam (FIB) machining tool) removes material from the surface of the wafer above the buried defect until the buried defect is made visible to an electron-beam based measurement system. The electron-beam based measurement system is subsequently employed to further analyze the defect.

A physical mark is generated near the location of the defect discovered by the inspection tool. In general, the physical mark may be generated in many different ways. In some embodiments, the physical mark is generated by a pulsed laser. The wavelength, power, and pulse duration of the laser are selected to create a small mark on the wafer surface. In some examples, the laser energy is absorbed by the top layers of the wafer to create a mark at the surface. In some other examples, the laser energy is absorbed by underlying layers or the substrate. In these examples, a bump or other material disturbance is generated at the surface.

In some embodiments, the physical mark is generated by a mechanical probe (e.g., stylus, indenter, atomic force microscope (AFM) probe, etc.) that generates the mark on the surface of the wafer by mechanical contact.

In some embodiments, the physical mark is generated by an electron beam source configured to bombard the wafer with electrons to generate heat. In some examples, the electron beam disassociates organic materials present in the vacuum chamber in the vicinity of the electron beam. The disassociated materials are transported by the electron beam to the surface of the wafer where they adhere to the surface, leaving a mark. In other embodiments, the beam is focused below the surface of the wafer and the heat generated causes a bump to form on the surface of the wafer.

In general, the physical shape and size of a mark are conducive to fast image acquisition and accurate image-based location of the mark relative to a buried defect. The mark is located close enough to an associated buried defect so that both the mark and the buried defect are within the field of view of the inspection system and the imaging system utilized in conjunction with the material removal tool. It is preferable that the shape of the mark be symmetric.

Although, a single mark may be associated with a particular buried defect, it is preferable to generate more than one mark near each buried defect. In some embodiments, two or more marks are associated with a buried defect. In this manner, a buried defect can be accurately located with respect to the marks in two dimensions. In some embodiments, three or more marks are located around a buried defect such that an imaginary polygon having a vertex at each mark encloses the buried defect.

In a preferred embodiment, the marking tool is integrated with the inspection tool in a common wafer processing system so that a buried defect is discovered, marked, and located relative to the mark by the same wafer processing system.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
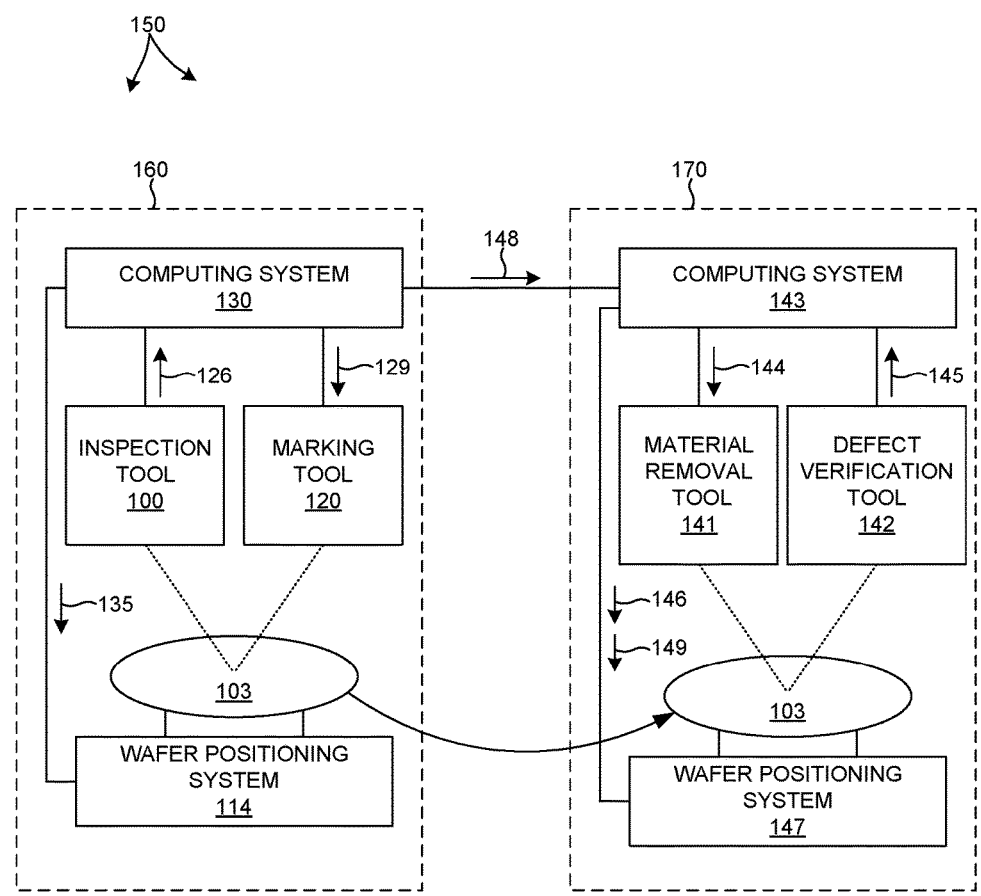
FIG. 1 is a simplified schematic view of one embodiment of a defect locating system 150 configured to perform detection, marking, and locating of defects of interest (DOI) buried in semiconductor structures.

Reference will now be made in detail to background examples and some embodiments of the invention, examples of which are illustrated in the accompanying drawings.

Methods and systems for accurately locating buried defects previously detected by an optical or x-ray inspection system are described herein.

In one aspect, a physical mark is made on the surface of a wafer near a buried defect detected by an inspection system. In addition, the inspection system is employed to accurately measure the distance between the detected defect and the physical mark in at least two dimensions. The wafer, an indication of the nominal location of the mark, and an indication of the distance between the detected defect and the mark are transferred to a defect verification tool. In some embodiments, the defect verification tool is an x-ray based measurement system. In some embodiments, the defect verification tool is an electron beam based measurement system. In some of these embodiments, a material removal tool (e.g., a focused ion beam (FIB) machining tool) removes material from the surface of the wafer above the buried defect until the buried defect is made visible.

In one embodiment, a FIB tool uncovers a buried defect, making the defect visible to an electron-beam based measurement system. The electron-beam based measurement system is subsequently employed to further analyze and verify the defect. An electron-beam based measurement system cannot directly detect or verify defects buried in relatively thick semiconductor structures. In some examples, defects that are buried at least fifty nanometers below the surface of a structure are not visible to an electron-beam based measurement system. In some examples, defects that are buried at least three micrometers below the surface of a structure are not visible to an electron-beam based measurement system. But, the system is able to accurately locate a physical mark located on the surface of the wafer. After accurately locating the physical mark, the electron-beam based system is able to accurately locate the buried defect based on the distance between the detected defect and the physical mark received from the inspection system. In this manner, the electron-beam based system is able to accurately locate the defect without being able to "see" the defect. This speeds up the process of material removal and defect verification greatly.

By accurately marking the position of buried defects discovered by inspection, subsequent material removal and electron beam based measurement of the buried defects is streamlined, saving a significant amount of time. This is particularly important in the inspection of 3D NAND structures, where the layer stack is 3 um thick or thicker, and other vertical memory and logic architectures such as resistive-RAM, cross-point, Fin-FETs, gate-all-around, and nanowire transistor structures. These defects would otherwise be invisible to electron beam based measurement tools such as electron beam inspection (EBI) tools, electron beam review (EBR) tools, tools incorporating scanning electron microscopy (SEM), etc.

FIG. 1 is a simplified schematic view of one embodiment of a defect locating system 150 configured to perform detection, marking, and locating of defects of interest (DOI) buried in semiconductor structures. Defect locating system 150 includes an inspection tool 100, a marking tool 120, a material removal tool 141, and a defect verification tool 142. In some embodiments, the defect verification tool is an electron beam based analysis tool. In some other embodiments, the defect verification tool is an x-ray based analysis tool. In these embodiments, a material removal tool may not be necessary to make the buried defect visible to the x-ray based analysis tool. Thus, a material removal tool is optional.

In the embodiment depicted in FIG. 1, defect locating system 150 includes a wafer processing system 160 that includes inspection tool 100 and marking tool 120. Defect locating system 150 also includes a wafer processing system 170 that includes material removal tool 141 and electron beam analysis tool 142. In general, however, inspection tool 100, marking tool 120, material removal tool 141, and electron beam analysis tool 142 may be integrated into a single wafer processing tool or separated into different wafer processing systems individually, or in any combination.

Wafer processing system 160 includes a wafer positioning system 114 to accurately position wafer 103 with respect to inspection tool 100 and marking tool 120 for inspection and marking, respectively. Computing system 130 coordinates the inspection and marking processes (e.g., via signals 126 and 129, etc.), and performs analyses, data handling, and communication tasks. Similarly, wafer processing system 170 includes a wafer positioning system 147 to accurately position wafer 103 with respect to material removal tool 141 and electron beam analysis tool 142 for material removal and defect location and review, respectively. Computing system 143 coordinates the material removal and review processes, performs analyses, and performs data handling and communication tasks.

In one aspect, an inspection of wafer 103 is performed by inspection tool 100 to discover buried defects. In some embodiments, inspection tool 100 is an optical inspection system. However, in some other embodiments, inspection tool 100 is an x-ray inspection system or a combined optical and x-ray based inspection system.

Figure 2:
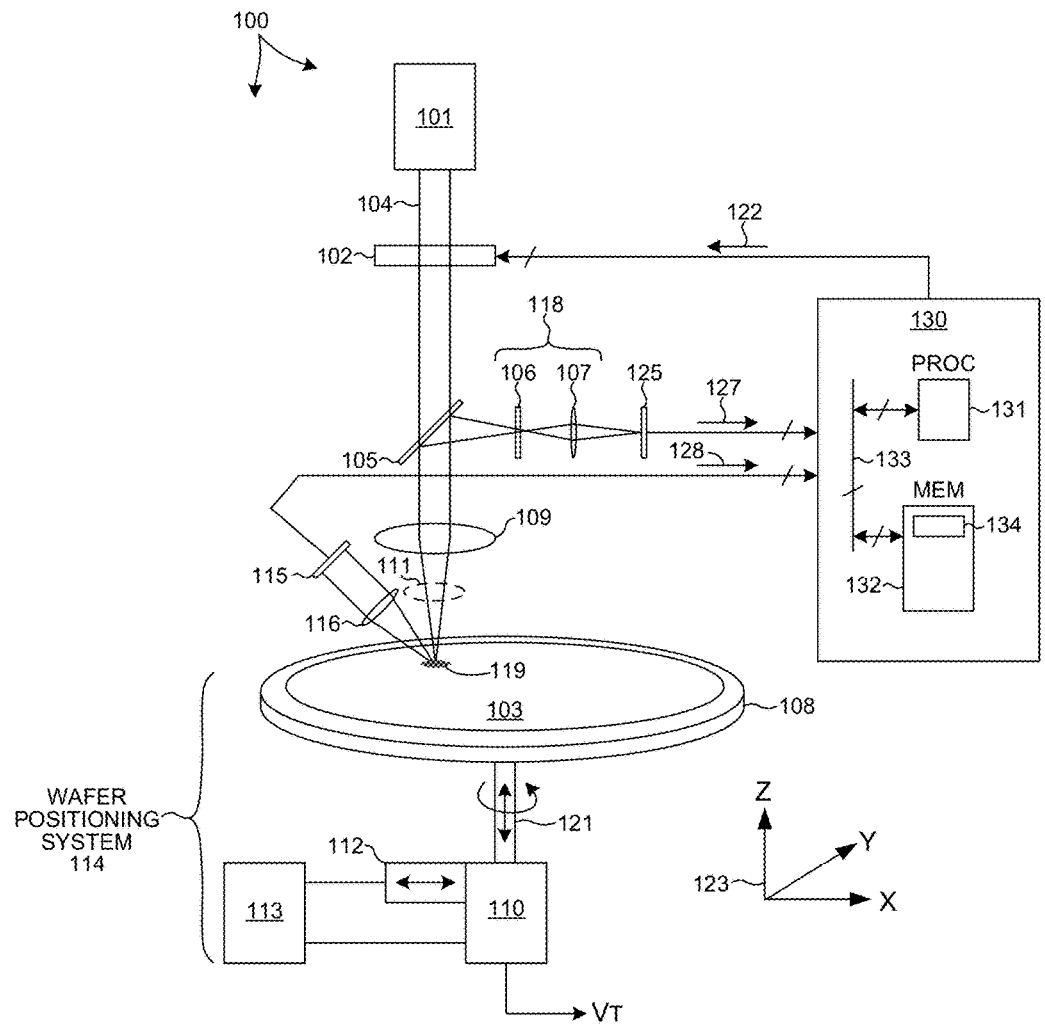
FIG. 2 is a simplified schematic view of one embodiment of an optical inspection system configured to perform detection of defects of interest (DOI) and measurements of distance between DOIs and associated physical marks on the surface of a semiconductor wafer.

FIG. 2 is a simplified schematic view of one embodiment of an optical inspection system configured to perform detection of defects of interest (DOI) on semiconductor wafers. For simplification, some optical components of the system have been omitted. By way of example, folding mirrors, polarizers, beam forming optics, additional light sources, additional collectors, and detectors may also be included. All such variations are within the scope of the invention described herein. The inspection system described herein may be used for inspecting patterned wafers and reticles.

As illustrated in FIG. 2, wafer 103 is illuminated by a normal incidence beam 104 generated by one or more illumination sources 101. Alternatively, the illumination subsystem may be configured to direct the beam of light to the specimen at an oblique angle of incidence. In some embodiments, system 100 may be configured to direct multiple beams of light to the specimen such as an oblique incidence beam of light and a normal incidence beam of light. The multiple beams of light may be directed to the specimen substantially simultaneously or sequentially.

Illumination source 101 may include, by way of example, a broad band laser sustained plasma light source, a laser, a supercontinuum laser, a diode laser, a helium neon laser, an argon laser, a solid state laser, a diode pumped solid state (DPSS) laser, a xenon arc lamp, a gas discharging lamp, an LED array, and an incandescent lamp. The light source may be configured to emit near monochromatic light or broadband light. In some embodiments, the illumination subsystem may also include one or more spectral filters that may limit the wavelength of the light directed to the specimen. The one or more spectral filters may be bandpass filters and/or edge filters and/or notch filters. Illumination may be provided to the specimen over any suitable range of wavelengths. In some examples, the illumination light includes wavelengths ranging from 260 nanometers to 900 nanometers. In some examples, illumination light includes wavelengths greater than 900 nanometers (e.g., extending to 2,500 nanometers) to capture defects in high aspect ratio structures.

Beam 104 generated by illumination source 101 is directed to a beam splitter 105. Beam splitter 105 directs the beam to objective lens 109. Objective lens 109 focuses the beam 111 onto wafer 103 at incident spot 119. Incident spot 119 is defined (i.e., shaped and sized) by the projection of light emitted from illumination source 101 onto the surface of wafer 103. In general, the beam 111 that is incident on wafer 103 may differ from the light emitted by illumination source 101 in one or more ways, including polarization, intensity, size and shape, etc.

System 100 includes collection optics 116 and 118 to collect the light scattered and/or reflected by wafer 103 and focus that light onto detector arrays 115 and 125, respectively. The outputs 128 and 127 of detectors 115 and 125, respectively, are communicated to computing system 130 for processing and determining the presence of defects and their locations. In one example, signals 126 depicted in FIG. 1 include output signals 127, 128, or a combination thereof.

Any of collection optics 116 and 118 may be a lens, a compound lens, or any appropriate lens known in the art. Alternatively, any of collection optics 116 and 118 may be a reflective or partially reflective optical component, such as a mirror. In addition, although particular collection angles are illustrated in FIG. 2, it is to be understood that the collection optics may be arranged at any appropriate collection angle. The collection angle may vary depending upon, for example, the angle of incidence and/or topographical characteristics of the specimen.

Each of detectors 115 and 125 generally function to convert the scattered light into an electrical signal, and therefore, may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes and photomultiplier tubes (PMTS) may be used, depending on the amount of light available for inspection and the type of inspection being performed. Each detector may include only one sensing area, or possibly several sensing areas (e.g., a detector array, an array of discrete PMT detectors, a multi-anode PMT, etc.).

System 100 can use various imaging modes, such as bright field and dark field modes. For example, in one embodiment, detector 125 generates a bright field image. As illustrated in FIG. 2, some amount of light scattered from the surface of wafer 103 at a narrow angle is collected by objective lens 109. This light passes back through objective lens 109 and impinges on beam splitter 105. Beam splitter 105 transmits a portion of the light to collection optics 118, which in turn focuses the light onto detector 125. In this manner a bright field image is generated by detector array 125. Collection optics 118 includes imaging lens 107 that images the reflected light collected by objective lens 109 onto detector array 140. An aperture or Fourier filter 106 is placed at the back focal plane of objective lens 109. Various imaging modes such as bright field, dark field, and phase contrast can be implemented by using different apertures or Fourier filters. U.S. Pat. Nos. 7,295,303 and 7,130,039, which are incorporated by reference herein, describe these imaging modes in further detail. In another example, detector 115 generates dark field images by imaging scattered light collected at larger field angles. U.S. Pat. No. 6,208,411, which is incorporated by reference herein, describes these imaging modes in further detail.

System 100 also includes various electronic components (not shown) needed for processing the reflected and/or scattered signals detected by any of detectors 115 and 125. For example, system 100 may include amplifier circuitry to receive output signals from any of detectors 115 and 125 and to amplify those output signals by a predetermined amount and an analog-to-digital converter (ADC) to convert the amplified signals into a digital format suitable for use within processor 131. In one embodiment, the processor may be coupled directly to an ADC by a transmission medium. Alternatively, the processor may receive signals from other electronic components coupled to the ADC. In this manner, the processor may be indirectly coupled to the ADC by a transmission medium and any intervening electronic components.

In the embodiment illustrated in FIG. 1, wafer positioning system 114 moves wafer 103 under beam 111 based on command signals 135 received from computing system 130. Wafer positioning system 114 includes a wafer chuck 108, motion controller 113, a rotation stage 110, translation stage 112, and z-translation stage 121. Z-translation stage 121 is configured to move wafer 103 in a direction normal to the surface of wafer 103 (e.g., the z-direction of coordinate system 123). Translation stage 112 and rotation stage 110 are configured to move wafer 103 in a direction parallel to the surface of wafer 103 (e.g., the x and y directions of coordinate system 123). In some other embodiments, wafer 103 is moved in the in-plane directions (e.g., x and y directions) by the coordinated motion of multiple translation stages.

Wafer 103 is supported on wafer chuck 108. In some embodiments, wafer 103 is located with its geometric center approximately aligned with the axis of rotation of rotation stage 110. In this manner, rotation stage 110 spins wafer 103 about its geometric center at a specified angular velocity, $\omega$, within an acceptable tolerance. In addition, translation stage 112 translates the wafer 103 in a direction approximately perpendicular to the axis of rotation of rotation stage 110 at a specified velocity, $V_T$. Motion controller 113 coordinates the spinning of wafer 103 by rotation stage 110 and the translation of wafer 103 by translation stage 112 to achieve a desired in-plane scanning motion of wafer 103 within inspection system 100. In addition, motion controller 113 coordinates the movement of wafer 103 by translation stage 121 to achieve a desired out-of-plane scanning motion of wafer 103 within inspection system 100.

Wafer 103 may be positioned relative to the optical subsystems of inspection system 100 in a number of different modes. In an inspection mode, wafer 103 is repeatedly scanned in the lateral directions (e.g., x-direction and y-direction) at different z-positions. In some examples, wafer 103 is scanned at ten or more different depths of focus through a layered structure that is at least three micrometers thick. In a defect review mode, wafer 103 is positioned in a fixed position in the x-direction and y-directions, while scanning in the z-direction. In this manner, images are generated based on measurement data at a fixed lateral position of wafer 103 over a range of depths within the structure under measurement. Defect review mode is typically employed to perform more detailed investigation of defects (e.g., higher image resolution, higher focal depth resolution, or both).

In some embodiments, system 100 may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

As depicted in FIG. 2, inspection system 100 includes an illumination power attenuator 102 that controls the illumination power delivered to wafer 103. In some other embodiments, the illumination power density attenuator is a beam shaping element that resizes the illumination spot 119 to reduce the illumination power density delivered to wafer 103. In some other embodiments, a combination of illumination power reduction and beam sizing is employed to reduce the illumination power density delivered to wafer 103. As depicted in FIG. 2, computing system 130 communicates a control signal 122 to illumination power attenuator 102 to control illumination power based on images detected by any of detectors 115 and 125. In general, illumination power attenuator 102 is optional.

In some examples, a three dimensional image of a thick semiconductor structure is generated from a volume measured in two lateral dimensions (e.g., parallel to the wafer surface) and a depth dimension (e.g., normal to the wafer surface. In the embodiment depicted in FIG. 2, computing system 130 arranges the outputs from one or more of the measurement channels (e.g., from one or more of detectors 115 and 125) into a volumetric data set that corresponds to the measured volume.

In a further aspect, defects are identified based on an analysis of light detected from wafer 103. In some embodiments, images are plotted and the resulting renderings are read by an operator who selects defects of interest. In one embodiment, inspection system 100 includes peripheral devices useful to accept inputs from an operator (e.g., keyboard, mouse, touchscreen, etc.) and display outputs to the operator (e.g., display monitor). Input commands from an operator may be used by processor 131 to flag defects. Images of an inspected volume may be graphically presented to an operator on a display monitor.

In some embodiments, signals generated by the detector(s) are processed algorithmically by processor 131 to identify and classify defects of interest. The processor may include any appropriate processor known in the art. In addition, the processor may be configured to use any appropriate defect detection and classification algorithm or method known in the art. For example, the processor may use a die-to-database comparison, a three-dimensional filter, a clustering algorithm such as principal component analysis or spectral clustering, a thresholding algorithm, a deep learning algorithm, or any other suitable algorithm to detect and classify defects on the specimen.

In another aspect, the nominal location of a defect of interest is determined based on an analysis of one or more images of the thick semiconductor structure, including the defect. In this manner, the position of a defect with respect to one or more reference features of the wafer is measured (e.g., coordinates of the defect with respect to a fiducial or other reference geometry located on the wafer).

In some examples, the nominal defect position is determined based on peak defect signals within one or more images of the defect. In other examples, the nominal defect position is determined by comparing one or more measured images with one or more reference images of the semiconductor structure under inspection.

The nominal defect position can used to locate the defect later for further analysis (e.g., analysis by a focused ion beam system, EBI system, x-ray based system, etc.). However, typically, this requires transferring the wafer and the nominal position coordinates to another tool for analysis and material removal, if necessary. Positioning errors introduced by the wafer transfer, errors in the translation of the nominal position coordinates, etc., typically result in positioning errors on the order of a micrometer. This makes it difficult to accurately locate the actual defect location for subsequent processing.

In another aspect, a physical mark is generated near the location of the defect discovered by the inspection tool (e.g., inspection tool 100). As depicted in FIG. 1, wafer processing system 160 includes a marking tool 120 configured to physically mark the surface of the wafer near the location of the defect. The mark on the surface is visible to imaging systems commonly utilized in semiconductor fabrication equipment. In this manner, the mark associated with the buried defect can be easily located in another wafer processing system, such as wafer processing system 170.

Figure 3:
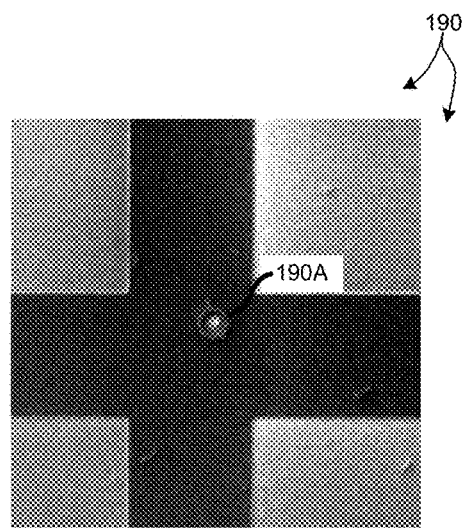
FIG. 3 depicts a scanning electron microscope (SEM) image 190 of a mark 190A generated on the surface of a wafer by a pulsed laser.
Figure 4:
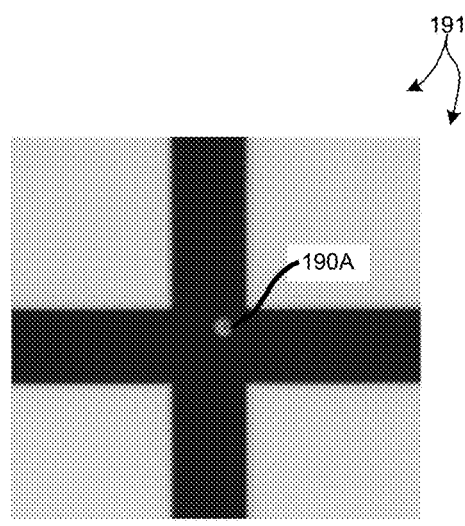
FIG. 4 depicts an image 191 of mark 190A. Image 191 is generated by a broadband bright field imaging system, such as inspection tool 100 depicted in FIG. 2.

In general, the physical mark can be generated in many different ways. In some embodiments, marking tool 120 includes a pulsed laser. The wavelength, power, and pulse duration of the laser are selected to create a small mark on the wafer surface. In some examples, pulsed lasers having wavelengths at 256 nanometers, 355 nanometer, or 532 nanometers may be utilized to effectively mark the surface of a wafer. In some examples, the laser energy is absorbed by the top layers of the wafer to create a mark at the surface. In some other examples, the laser energy is absorbed by underlying layers or the substrate. In these examples, a bump or other material disturbance is generated at the surface. FIG. 3 depicts a scanning electron microscope (SEM) image 190 of a circular mark 190A generated on the surface of a wafer by a pulsed laser. The mark is approximately 750 nanometers in diameter. FIG. 4 depicts an image 191 of mark 190A generated by a broadband bright field imaging system, such as inspection tool 100 depicted in FIG. 2. As depicted in FIGS. 3 and 4, a well-defined mark is generated at the surface of the wafer, and this mark is visible by conventional electron beam based imaging systems and a broadband bright field imaging system, such as inspection tool 100 depicted in FIG. 2.

Figure 5:
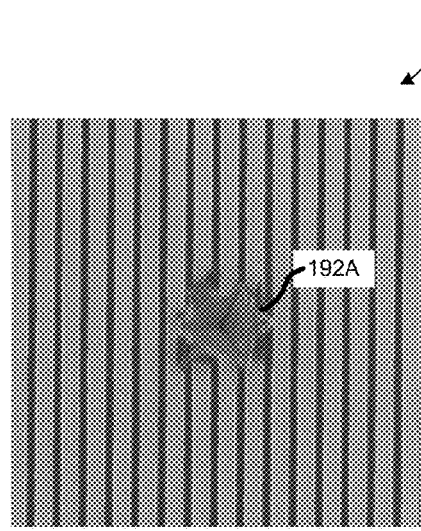
FIG. 5 depicts a SEM image 192 of a mark 192A generated by a diamond tipped, corner cube indenter.
Figure 6:
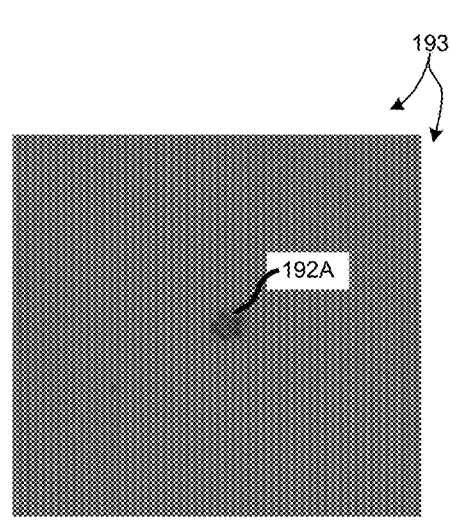
FIG. 6 depicts an image 193 of mark 192A. Image 193 is generated by a broadband bright field imaging system, such as inspection tool 100 depicted in FIG. 2.

In some embodiments, marking tool 120 includes a mechanical probe (e.g., stylus, indenter, atomic force microscope (AFM) probe, etc.) that generates a mark on the surface of the wafer by mechanical contact. FIG. 5 depicts a SEM image 192 of a mark 192A generated by a diamond tipped, corner cube indenter. The mark is approximately 700 nanometers at its maximum lateral extent. As depicted in image 192, a well-defined triangular shaped mark is generated at the surface of the wafer. FIG. 6 depicts an image 193 of mark 192A generated by a broadband bright field imaging system, such as inspection tool 100 depicted in FIG. 2. As depicted in FIGS. 5 and 6, a well-defined mark is generated at the surface of the wafer, and this mark is visible by conventional electron beam based imaging systems and a broadband bright field imaging system, such as inspection tool 100 depicted in FIG. 2. In some other embodiments, a mechanical indenter may be employed to generate a mark of approximately one micrometer. In general, it is preferable for the marks to include lines or shapes, such as an "x" shape or a "+" shape, so that a more repeatable measurement of the location of the mark can be made.

In some embodiments, marking tool 120 includes an electron beam source configured to bombard the surface of the wafer with electrons to generate heat. In some examples, the electron beam disassociates organic materials present in the vacuum chamber in the vicinity of the electron beam. The disassociated materials are transported by the electron beam to the surface of the wafer where they adhere to the surface, leaving a mark. In other embodiments, the beam is focused below the surface of the wafer and the heat generated causes a bump to form on the surface of the wafer.

In a preferred embodiment, marking tool 120 is integrated with inspection tool 100 in a common wafer processing system 160 (shared wafer positioning system and computing system). It is advantageous to integrate the marking tool with the inspection tool because the same wafer processing system is used to discover the buried defect, mark the wafer, and precisely estimate the distance between the mark and the buried defect without transferring the wafer to another system. Otherwise, the wafer must be transferred to another system for marking, and then the wafer must either be transferred back to the inspection system to re-measure the buried defect and the mark to determine the distance between the two, or the marking system must include another inspection system suitable for determining the location of the buried defect, the mark, and the distance between them.

In general, however, marking tool 120 may be integrated with another wafer processing system, such as wafer processing system 170, a stand-alone wafer marking system, or another system. In an embodiment where marking tool 120 is integrated with wafer processing system 170, it may be preferable to utilize the electron beam associated with electron beam analysis tool 142 to generate the mark on the wafer. In another embodiment where marking tool 120 is integrated with wafer processing system 170, it may be preferable to utilize material removal tool 141 to generate the mark on the wafer. In one example, material removal tool 141 employs a focused ion beam to effectively mark the surface of the wafer near a buried defect. In another example, the focused ion beam is used to deposit small amounts of metal (e.g., platinum) on the wafer surface to effectively mark the surface of the wafer near a buried defect. In some embodiments, system 170 includes marking tool 120 and an inspection system suitable for determining the location of the buried defect, the mark, and the distance between them. However, this approach may introduce undesirable, additional cost and complexity.

In general, the physical shape and size of a mark should be conducive to fast image acquisition and accurate image-based location of the mark relative to a buried defect. For example, a mark should be located close enough to an associated buried defect so that both the mark and the buried defect are within the field of view of the inspection system and the imaging system utilized in conjunction with material removal tool 141. In one example, a scanning electron microscope (SEM) is utilized with material removal tool 141. In some embodiments, one or more marks associated with a particular buried defect are located within five micrometers of a buried defect. For example, a mechanical indenter that generates a mark of approximately one micrometer may be employed to mark the defect. Such a large mark should be located a few micrometers away from the buried defect (e.g., four micrometers) to avoid disturbing the buried defect. In some embodiments, one or more marks are located within two micrometers of the buried defect. In some embodiments, one or more marks are located within one micrometer of the buried defect. For example, a FIB tool that generates a mark of approximately one hundred nanometers may be employed to mark the defect. Such a small mark can be located approximately one micrometer, or less, from the buried defect to avoid disturbing the buried defect.

It is preferable that the shape of the mark be symmetric (e.g., an "x" shape, a "+" shape, etc.). The relative location of symmetric marks and defect signals can be measured much more accurately than the size of the optical point-spread-function (PSF) of inspection tool 100. In a typical optical based inspection system, the PSF is approximately 0.5-0.75 micrometers. In some other examples, the PSF of an optical based inspection system can be as small as 0.3 micrometers or as large as 1.0 micrometer, depending on the wavelengths and apertures employed. In some examples, if the marks are smaller than approximately one micrometer, but not smaller than the PSF of inspection tool 100, the relative location of symmetric marks and defect signals can be measured with an accuracy of less than 100 nanometers. In some examples, the relative location of symmetric marks and defect signals can be measured with an accuracy of less than 20 nanometers.

Figure 7A:
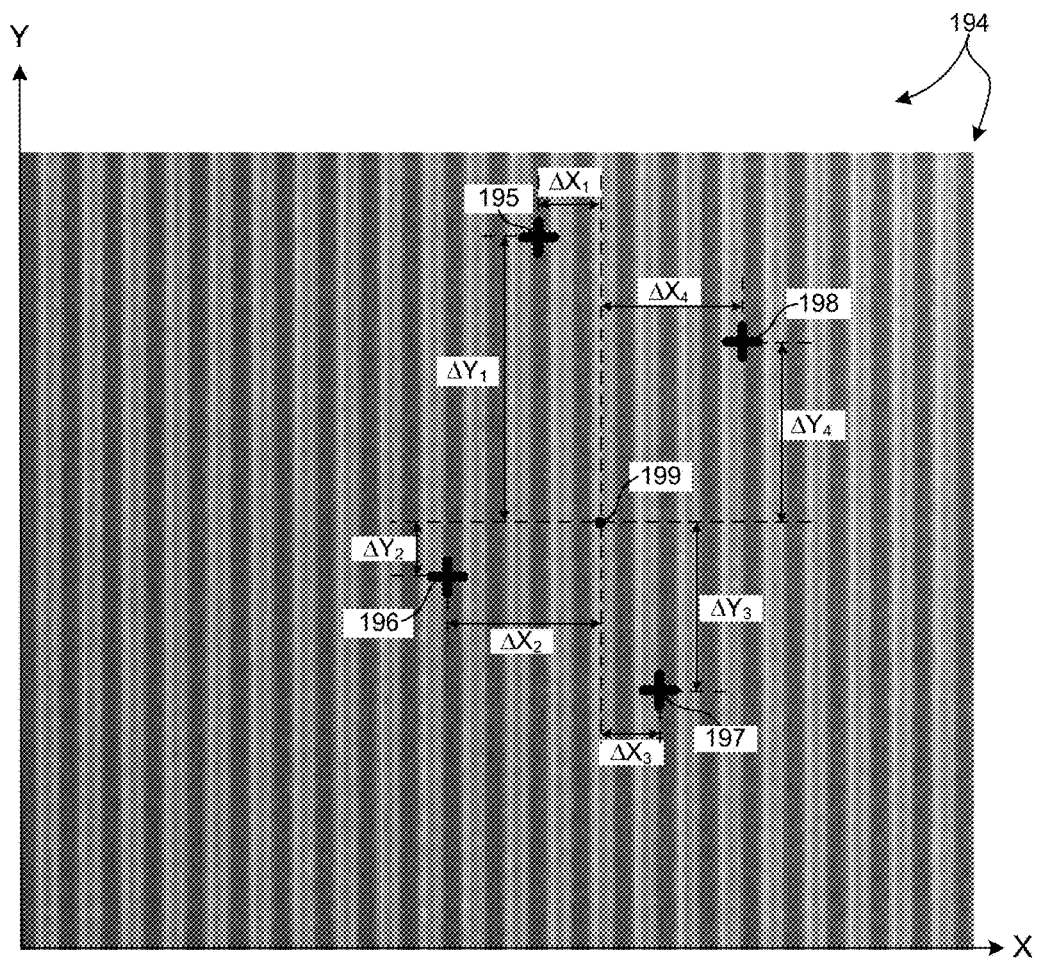
FIG. 7A depicts an image 194 of four exemplary marks 195-198.

Although, a single mark may be associated with a particular buried defect, it is preferable to generate more than one mark near each buried defect. In some embodiments, two or more marks are associated with a buried defect. In some embodiments, three or more marks are located around a buried defect such that an imaginary polygon having a vertex at each mark encloses the buried defect. FIG. 7A depicts an illustration of four marks 195-198 generated by a mechanical indenter. In this example, the four marks are located around a buried defect 199 in a box shape pattern with the defect 199 approximately centered in the box shape pattern.

In another aspect, the marked wafer is re-measured by inspection system 100 to detect both the buried defect and the associated marks. The image is analyzed to determine the locations of the buried defect and the associated marks and estimate the distance between the two in at least two dimensions. It is not necessary to determine the absolute coordinates of the defect or the mark to high accuracy. In other words, it is not necessary to accurately locate the defect and associated marks with respect to wafer fiducials or other reference geometry. It is only necessary to locate the defect and associated marks with respect to wafer fiducials or other reference geometry with sufficient accuracy to enable an inspection system on board wafer processing system 170 (e.g., material removal tool 141, defect verification tool 142 or another inspection system) to quickly locate the mark. The required accuracy is on the order of micrometers, not nanometers. However, the distance between the buried defect and the associated marks should be estimated with high accuracy (e.g., measurement accuracy less than 100 nanometers). In this manner, the buried defect (which is invisible) can be located with very high accuracy, once the associated marks (which are visible) are found.

In some embodiments, material removal tool 120 is a focused ion beam (FIB) machining tool that removes material in slices that are 20 nanometers wide. If the relative location accuracy is poor, e.g., one micrometer, then fifty slices may be required to uncover the buried defect. However, if the relative location accuracy is good, e.g., 100 nanometers, then only five slices may be required to uncover the buried defect. In this manner, the throughput of electron beam analysis of buried defects discovered by optical inspection is greatly improved.

FIG. 7A depicts an image 194 with an illustration of four marks 195-198 generated by a mechanical indenter. In addition, FIG. 7A depicts the location 199 of a buried defect estimated by inspection system 100. Each mark may be located within image 194 in a number of different ways. In some embodiments, a mark is manually located within an image based coordinate frame. In these embodiments, a zoomed image of each mark is presented to an operator who manually selects a pixel associated with the location of the mark. In one example, an operator may locate a cursor over the image and tag a location that the operator feels is closest to a centroid of the mark or some other visually identifiable feature.

In some embodiments, the buried defect and associated marks are automatically located within an image based coordinate frame. In some examples, each of the measured point spread functions is fit to a basis function (e.g., Gaussian function). The centroid or peak of the fitted functions is employed to accurately determine the locations of the buried defects and associated marks in the image frame.

After the buried defect and associated marks are accurately located within an image, the distance is calculated between the buried defect and each of the associated marks in at least two dimensions (i.e., at least two dimensions parallel to the image plane). For example, as depicted in FIG. 7A, the distance, •$X_1$, denotes the distance between the centroid of mark 195 and the centroid of the buried defect 199 in the x-direction, and the distance, $\Delta Y_1$, denotes the distance between the centroid of mark 195 and the centroid of the buried defect 199 in the x-direction. Similarly, the distances, $\Delta X_2$, and, $\Delta Y_2$, denote the distances between the centroid of mark 196 and the centroid of the buried defect 199 in the x-direction and the y-direction, respectively. The distances, $\Delta X_3$, and, $\Delta Y_3$, denote the distances between the centroid of mark 197 and the centroid of the buried defect 199 in the x-direction and the y-direction, respectively. The distances, $\Delta X_4$, and, $\Delta Y_4$, denote the distances between the centroid of mark 198 and the centroid of the buried defect 199 in the x-direction and the y-direction, respectively.

In another aspect, the wafer, the distance between each buried defect and associated marks, and the nominal locations of the marks are transferred to a wafer processing system that includes a material removal tool. The wafer processing tool uses the nominal locations of the marks to locate the marks on the wafer. After locating the marks, the wafer processing tool uses the distance between a buried defect and associated marks to accurately locate the buried defect. In a further aspect, material removal tool removes enough wafer material above the buried defect to enable an electron beam based imaging system to measure the buried defect.

As depicted in FIG. 1, wafer 103 is transferred to wafer processing system 170. In addition, signals 148 indicative of the distance between each buried defect and associated marks and the nominal locations of the marks are communicated from wafer processing tool 160 to wafer processing tool 170. In some examples, signals 148 are communicated as part of a KLA results file (KLARF file).

Computing system 143 communicates control commands 146 to wafer positioning system 147 to locate wafer 103 such that the marks associated with a particular buried defect are within the field of view of an imaging system such as an electron beam imaging system of wafer processing system 170. In this example, the control commands 146 are based at least in part on the nominal locations of the marks received from wafer processing system 160. In some examples, electron beam analysis tool 142 is the imaging system employed to locate the marks on wafer 103. In some other examples, another imaging system integrated with wafer processing system 170 is employed to locate the marks on wafer 103.

Figure 7B:
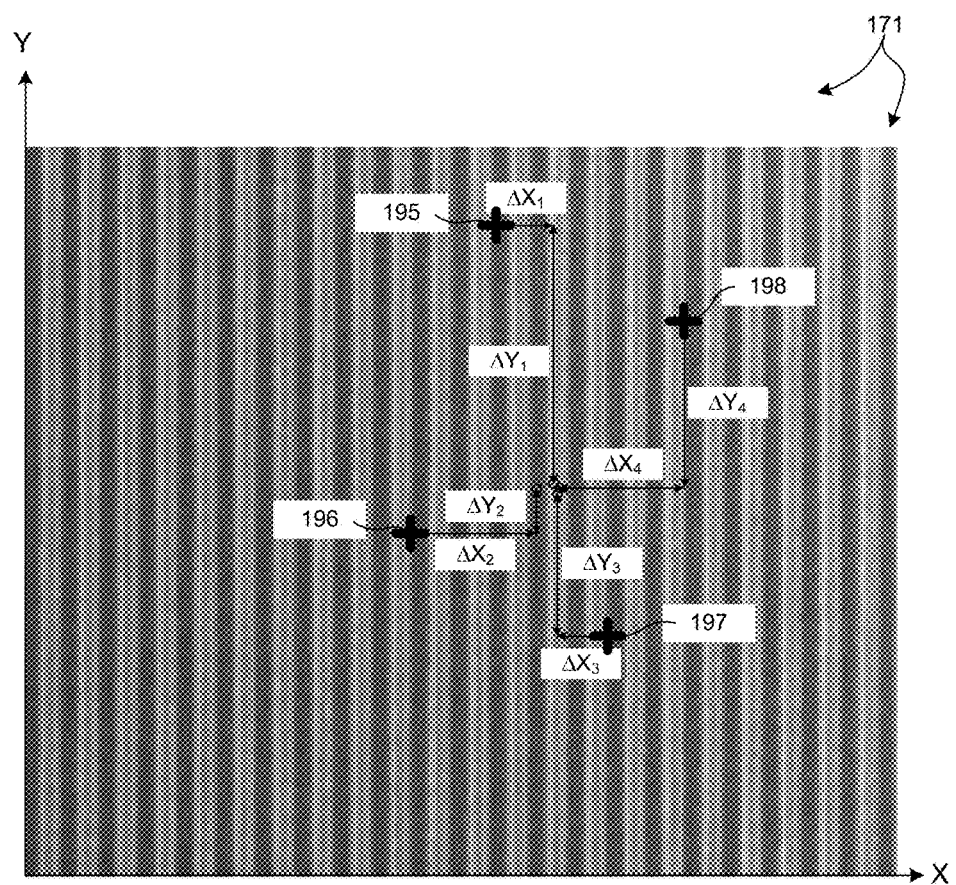
FIG. 7B depicts an image 171 of marks 195-198 depicted in FIG. 7A.

FIG. 7B depicts an image 171 of marks 195-198 depicted in FIG. 7A. Image 171 is collected, for example, by an imaging system of wafer processing system 170. Note that the imaging system is able to image the physical marks, but not the buried defect. As described with respect to FIG. 7A, each mark may be located within image 174 in a number of different ways. In some embodiments, a mark is manually located within an image based coordinate frame. In these embodiments, a zoomed image of each mark is presented to an operator who manually selects a pixel associated with the location of the mark. In one example, an operator may locate a cursor over the image and tag a location that the operator feels is closest to a centroid of the mark or some other visually identifiable feature.

In some embodiments, the marks are automatically located within an image based coordinate frame. In some examples, each of the measured point spread functions is fit to a basis function (e.g., Gaussian function). The centroid or peak of the fitted functions is employed to accurately determine the locations of the marks in the image frame.

After locating the marks, computing system 143 communicates control commands 149 to wafer positioning system 147 to locate wafer 103 such that the buried defect is located under material removal tool 141. In this example, control commands 149 are based at least in part on the offset distances between the buried defect and associated marks received from wafer processing system 160. After the marks are accurately located within image 171, the location of the buried defect is estimated based on the previously calculated relative offset distances between each mark and the buried defect (e.g., $\{\Delta X_1, \Delta Y_1\}$, $\{\Delta X_2, \Delta Y_2\}$, $\{\Delta X_3, \Delta Y_3\}$, $\{\Delta X_4, \Delta Y_4\}$). The estimated X and Y coordinates of the location of the buried defect may be calculated as function of the X and Y coordinates of each mark and the relative offset distances as illustrated by equation (1), where, i, is the number of marks associated with a particular buried defect.

$$X_{Defect_i} = X_{Mark_i} + \Delta X_i$$

$$Y_{Defect_i} = Y_{Mark_i} + \Delta Y_i \qquad (1)$$

Note the estimated location of the buried defect may vary from mark to mark. For example, as depicted by the small circles in FIG. 7B, the estimated location of the buried defect associated with each mark is slightly different. To arrive at a single estimated location of the buried defect, an average of the estimated defect coordinates may be calculated (e.g., $avg\{X_{Defecti}, Y_{Defecti}\}$ for all i). The aforementioned coordinate scheme is provided by way of non-limiting example. In general, many different schemes to estimate offset distances between marks and a buried defect and to estimate the location of a buried defect based on the locations of marks and the associated offset distances are contemplated within the scope of this patent document.

In addition, computing system 143 communicates control commands 144 to material removal tool 141 that cause material removal tool 141 to remove enough wafer material above the buried defect to enable electron beam analysis tool 142 to measure the buried defect.

In a further aspect, the buried defect is measured by a defect verification tool after wafer material located above the buried defect has been removed. As depicted in FIG. 1, electron beam analysis tool 142 inspects the buried defect (which is now visible to the electron beam based tool) and communicates measurement data 145 to computing system 143 for storage, further analysis, etc.

As depicted in FIG. 1, the uncovered defect is measured by an electron beam based analysis tool that is integrated with the material removal tool in the same wafer processing system. However, in general, the electron beam based analysis tool may be stand-alone tool or integrated in another wafer processing system.

Figure 9:
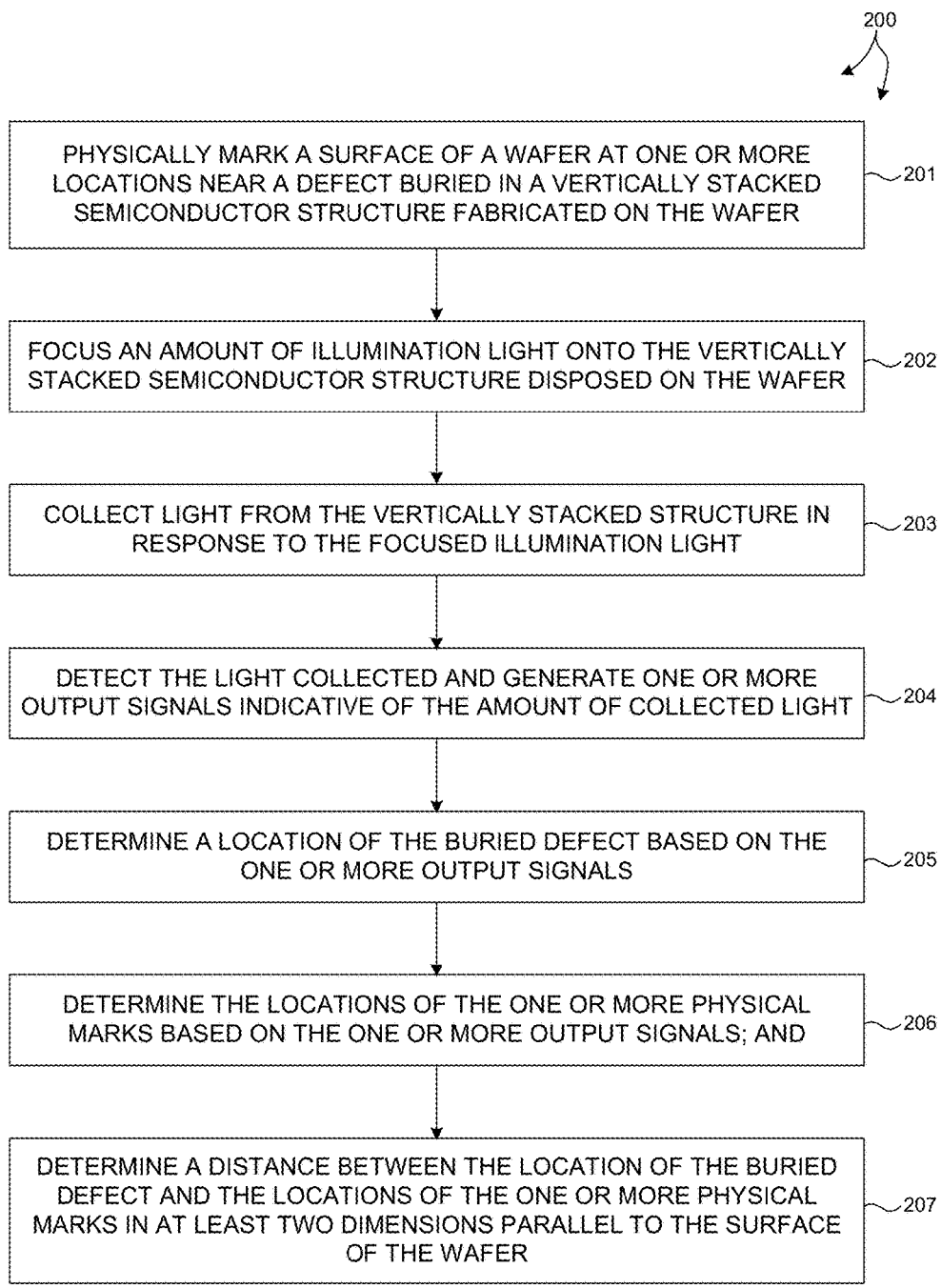
FIG. 9 illustrates a flowchart of an exemplary method 200 useful for marking and locating defects as described herein.

FIG. 9 illustrates a flowchart of an exemplary method 200 useful for accurately locating buried defects previously detected by an inspection system. In some non-limiting examples, defect locating system 150 described with reference to FIG. 1 is configured to implement method 200. However, in general, the implementation of method 200 is not limited by the specific embodiments described herein.

In block 201, a surface of a wafer is physically marked at one or more locations near a defect buried in a vertically stacked semiconductor structure fabricated on the wafer.

In block 202, an amount of illumination light is focused onto the vertically stacked semiconductor structure disposed on the wafer.

In block 203, light is collected from the vertically stacked structure in response to the focused illumination light.

In block 204, the collected light is detected and one or more output signals indicative of the amount of collected light are generated.

In block 205, a location of the buried defect is determined based on the one or more output signals.

In block 206, the locations of the one or more physical marks are determined based on the one or more output signals.

In block 207, a distance between the location of the buried defect and the locations of the one or more physical marks is determined in at least two dimensions parallel to the surface of the wafer.

In general, defect location system 150 may include peripheral devices useful to accept inputs from an operator (e.g., keyboard, mouse, touchscreen, etc.) and display outputs to the operator (e.g., display monitor). Input commands from an operator may be used by computing systems 130 and 143 to locate defects. The resulting defect locations may be graphically presented to an operator on a display monitor.

As depicted in FIG. 2, inspection tool 100 includes a processor 131 and an amount of computer readable memory 132. Processor 131 and memory 132 may communicate over bus 133. Memory 132 includes an amount of memory 134 that stores an amount of program code that, when executed by processor 131, causes processor 131 to execute the defect detection and location functionality described herein. Similarly, computing system 143 includes a processor and an amount of computer readable memory. The processor and memory may communicate over a bus. The memory includes an amount of memory that stores an amount of program code that, when executed by the processor, causes the processor to execute the defect detection and location functionality described herein.

In general, the marking and locating techniques described herein can be applied during research and development, production ramp, and high volume production phases of manufacture of semiconductor devices, and is applicable to any image-based measurement technique. Specifically, these techniques may be applied to optical and x-ray inspection modalities. In some examples, the defect detection and location techniques described herein are implemented using any of the broad band plasma based inspection tools manufactured by KLA-Tencor Corporation, such as the 29xx series tools, the 39xx series tool, or the 3D1 series tools. In some examples, the defect detection and location techniques described herein are implemented using any of the laser scanning based inspection tools manufactured by KLA-Tencor Corporation, such as the Puma 9xxx series tools. As described herein, the marking tool may be integrated with the inspection tool, or implemented on a separate module.

Regardless of the particular type of fabrication process, defects need to be detected in all levels of a multiple layer stack and as early as possible in the particular process. Certain inspection embodiments preferably include detection of defects throughout a stack, including the stack surface and throughout the various depths of a stack. For example, certain embodiments allow defects to be found at depths of up to about three micrometers. In another embodiment, defects can be detected at stack depths that are as large as about eight micrometers. The thickness of a vertical ONON or OPOP stack under inspection is limited only by the depth of penetration of the illumination light. Transmission through an oxide-nitride-oxide-nitride (ONON) or oxide-polysilicon-oxide-polysilicon (OPOP) stack is limited less by absorption at longer wavelengths. Thus, longer illumination wavelengths may be employed to effectively inspect very deep structures.

The marking and locating techniques described herein can be applied to complex, vertically stacked structures, including, but not limited to 3D negative-AND (NAND) gate memory devices. Although inspection systems and techniques are described herein as being applied to certain types of vertical NAND (VNAND) memory structures, it is understood that embodiments of the present invention may be applied to any suitable 3D or vertical semiconductor structures, such as NAND or NOR memory devices formed using terabit cell array transistors (TCAT), vertical-stacked array transistors (VSAT), bit cost scalable technology (BiCST), piped shaped BiCS technology (P-BiCS), etc. The vertical direction is generally a direction that is perpendicular to the substrate surface. Additionally, although particular fabrication steps, processes, and materials are described for forming such 3D structures, inspection embodiments may be applied at any point in the fabrication flow that results in multiple layers being formed on a substrate, and such layers may include any number and type of materials.

Figure 8:
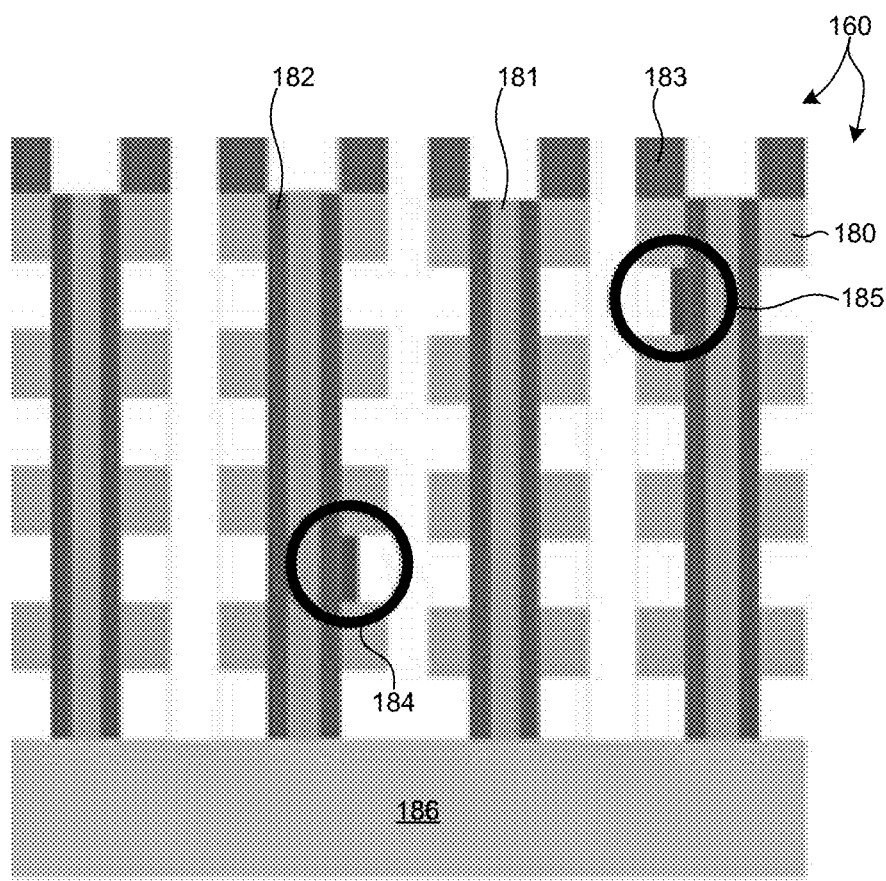
FIG. 8 depicts an illustration of a 3D NAND structure 160 at the silicon nitride removal step of the wafer production process.

FIG. 8 depicts a 3D NAND structure 160 at the silicon nitride (e.g., SiN or Si3N4) removal step of the wafer production process. Polysilicon structures 181 and Titanium nitride structures 182 extend vertically (e.g., normal to the surface of substrate 186) in the multi-layer 3D NAND structure. Layers of Silicon oxide 180 are spaced apart from one another by layers of Silicon nitride 183 that are subsequently etched away. The next step in the process is to grow tungsten in the space between the silicon oxide layers. However, as illustrated in FIG. 8, incomplete etching has left behind silicon nitride defects 184 and 185. The electronic device will not function with defects 184 and 185. Thus, it is important to measure this defect as early as possible in the fabrication process to prevent loss of time and resources associated with further processing of a device that is destined to fail.

Various embodiments are described herein for an inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern.

The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. In one example, a detector may include a fiber array. In one example, inspection system 100 may include more than one light source (not shown). The light sources may be configured differently or the same. For example, the light sources may be configured to generate light having different characteristics that can be directed to a wafer at the same or different illumination areas at the same or different angles of incidence at the same or different times. The light sources may be configured according to any of the embodiments described herein. In addition one of the light sources may be configured according to any of the embodiments described herein, and another light source may be any other light source known in the art. In some embodiments, an inspection system may illuminate the wafer over more than one illumination area simultaneously. The multiple illumination areas may spatially overlap. The multiple illumination areas may be spatially distinct. In some embodiments, an inspection system may illuminate the wafer over more than one illumination area at different times. The different illumination areas may temporally overlap (i.e., simultaneously illuminated over some period of time). The different illumination areas may be temporally distinct. In general, the number of illumination areas may be arbitrary, and each illumination area may be of equal or different size, orientation, and angle of incidence. In yet another example, inspection system 100 may be a scanning spot system with one or more illumination areas that scan independently from any motion of wafer 103. In some embodiments an illumination area is made to scan in a repeated pattern along a scan line. The scan line may or may not align with the scan motion of wafer 103. Although as presented herein, wafer positioning system 114 generates motion of wafer 103 by coordinated rotational and translational movements, in yet another example, wafer positioning system 114 may generate motion of wafer 103 by coordinating two translational movements. For example, wafer positioning system 114 may generate motion along two orthogonal, linear axes (e.g., X-Y motion). In such embodiments, scan pitch may be defined as a distance between adjacent translational scans along either motion axis.

Accordingly, various modifications, adaptations, and combinations of various features of the described embodiments can be practiced without departing from the scope of the invention as set forth in the claims.

What is claimed is:

1. A defect locating system comprising:
   a marking tool configured to physically mark a surface of a wafer at one or more locations near a defect buried in a vertically stacked semiconductor structure fabricated on the wafer; and
   an optical inspection tool comprising:
   an illumination source configured to generate an amount of illumination light;
   an illumination subsystem configured to focus the amount of illumination light at a vertically stacked semiconductor structure disposed on a wafer;
   a collection subsystem configured to collect light from the vertically stacked structure in response to the focused illumination light;
   a detector configured to detect the light collected and generate one or more output signals indicative of the amount of collected light; and
   a computing system configured to:
   receive the one or more output signals;
   determine a location of the buried defect based on the one or more output signals;
   determine the locations of the one or more physical marks based on the one or more output signals; and
   determine a distance between the location of the buried defect and the locations of the one or more physical marks in at least two dimensions parallel to the surface of the wafer.

2. The defect locating system of claim 1, further comprising:
   a material removal tool configured to remove material from the surface of the wafer; and
   a computing system configured to:
   receive an indication of the locations of the one or more physical marks and the distance between the location of the buried defect and the locations of the one or more physical marks; and
   communicate a command signal to the material removal tool that causes the material removal tool to remove material from the wafer at the location of the buried defect; and
   a defect verification tool configured to image the buried defect after removal of the material.

3. The defect locating system of claim 2, wherein the material removal tool is a focused ion beam machining tool.

4. The defect locating system of claim 1, wherein the marking tool and the optical inspection tool are integrated into a single wafer processing tool.

5. The defect locating system of claim 1, wherein the marking tool includes any of a laser, a mechanical scribe, and an electron beam.

6. The defect locating system of claim 1, wherein the surface of the wafer is physically marked at two or more locations near the buried defect.

7. The defect locating system of claim 1, wherein each of the one or more physical marks are located within five micrometers of the location of the buried defect.

8. The defect locating system of claim 1, wherein the distance between the location of the buried defect and the locations of the one or more physical marks is determined with a precision of less than one hundred nanometers.

9. The defect locating system of claim 1, wherein the buried defect is located at least fifty nanometers below the surface of the wafer.

10. The defect locating system of claim 1, wherein the vertically stacked semiconductor structure is a three dimensional NAND memory device.

11. The defect locating system of claim 1, wherein the illumination source of the optical inspection system is a broadband laser sustained plasma light source.

12. A method comprising:
physically marking a surface of a wafer at one or more locations near a defect buried in a vertically stacked semiconductor structure fabricated on the wafer with a marking tool;
focusing an amount of illumination light generated by an illumination source of an optical inspection tool onto the vertically stacked semiconductor structure disposed on the wafer;
collecting light from the vertically stacked structure in response to the focused illumination light with a collection subsystem of the optical inspection tool;
detecting the light collected and generating one or more output signals indicative of the amount of collected light with a detector of the optical inspection tool;
determining a location of the buried defect based on the one or more output signals;
determining the locations of the one or more physical marks based on the one or more output signals; and
determining a distance between the location of the buried defect and the locations of the one or more physical marks in at least two dimensions parallel to the surface of the wafer, wherein the determining of the location of the buried defect, the determining of the locations of the one or more physical marks, and the determining of the distance are performed by a computing system.

13. The method of claim 12, further comprising:
removing material from the surface of the wafer at the location of the buried defect based at least in part on the distance between the location of the buried defect and the locations of the one or more physical marks.

14. The method of claim 13, further comprising:
imaging the buried defect with an defect verification tool after removal of the material.

15. The method of claim 12, wherein the marking of the surface of the wafer involves any of a laser, a mechanical scribe, and an electron beam.

16. The method of claim 12, wherein the surface of the wafer is physically marked at two or more locations near the buried defect.

17. The method of claim 12, wherein each of the one or more physical marks are located within five micrometers of the location of the buried defect.

18. The method of claim 12, wherein the distance between the location of the buried defect and the locations of the one or more physical marks is determined with a precision of less than one hundred nanometers.

19. The method of claim 12, wherein the vertically stacked semiconductor structure is at least three micrometers thick and the buried defect is located at least fifty nanometers below the surface of the wafer.

20. A defect locating system comprising:
a marking tool configured to physically mark a surface of a wafer at one or more locations near a defect buried in a vertically stacked semiconductor structure fabricated on the wafer; and
an optical inspection tool comprising:
an illumination source configured to generate an amount of illumination light;
an illumination subsystem configured to focus the amount of illumination light at a vertically stacked semiconductor structure disposed on a wafer;
a collection subsystem configured to collect light from the vertically stacked structure in response to the focused illumination light;
a detector configured to detect the light collected and generate one or more output signals indicative of the amount of collected light; and
a computing system comprising:
one or more processors; and
a non-transitory, computer-readable medium storing instructions, that when executed by the one or more processors, cause the defect locating system to:
receive the one or more output signals;
determine a location of the buried defect based on the one or more output signals;
determine the locations of the one or more physical marks based on the one or more output signals; and
determine a distance between the location of the buried defect and the locations of the one or more physical marks in at least two dimensions parallel to the surface of the wafer.

21. The defect locating system of claim 20, further comprising:
a material removal tool configured to remove material from the surface of the wafer, the non-transitory, computer-readable medium further storing instructions, that when executed by the one or more processors, cause the defect locating system to:
receive an indication of the locations of the one or more physical marks and the distance between the location of the buried defect and the locations of the one or more physical marks; and
communicate a command signal to the material removal tool that causes the material removal tool to remove material from the wafer at the location of the buried defect; and
a defect verification tool configured to image the buried defect after removal of the material.

* * * * *